US012048616B2

(12) United States Patent
Melling

(10) Patent No.: US 12,048,616 B2
(45) Date of Patent: Jul. 30, 2024

(54) FIRST AID MEDICAL TREATMENT APPARATUS AND METHOD

(71) Applicant: Wade Melling, Cedar City, UT (US)

(72) Inventor: Wade Melling, Cedar City, UT (US)

( * ) Notice: Subject to any disclaimer, the term of this patent is extended or adjusted under 35 U.S.C. 154(b) by 559 days.

(21) Appl. No.: 16/882,434

(22) Filed: May 22, 2020

(65) Prior Publication Data
US 2020/0368084 A1 Nov. 26, 2020

Related U.S. Application Data

(60) Provisional application No. 62/851,621, filed on May 22, 2019.

(51) Int. Cl.
| | | |
|---|---|---|
| *A61F 17/00* | (2006.01) | |
| *A45C 11/00* | (2006.01) | |
| *A61B 17/132* | (2006.01) | |
| *A61F 5/37* | (2006.01) | |
| *A61F 13/0246* | (2024.01) | |
| *A61F 15/02* | (2006.01) | |
| *A61B 17/00* | (2006.01) | |
| *A61B 50/30* | (2016.01) | |
| *A61F 13/00* | (2006.01) | |

(52) U.S. Cl.
CPC ............ *A61F 15/02* (2013.01); *A45C 11/00* (2013.01); *A61B 17/132* (2013.01); *A61B 17/1325* (2013.01); *A61F 5/3738* (2013.01); *A61F 13/0253* (2013.01); *A61F 17/00* (2013.01); *A45C 2011/007* (2013.01); *A61B 2017/00951* (2013.01); *A61B 2050/3008* (2016.02); *A61B 2050/318* (2016.02); *A61F 2013/00106* (2013.01)

(58) Field of Classification Search
CPC ............ A61F 15/02; A61F 17/00; A61F 2013/00106; A45C 11/00; A45C 2011/007; A61B 17/132; A61B 2050/3008; A61B 2050/318
USPC .......................................... 206/570
See application file for complete search history.

(56) References Cited

U.S. PATENT DOCUMENTS

| | | | | |
|---|---|---|---|---|
| 5,117,981 | A * | 6/1992 | Crawford | A61B 50/30 206/370 |
| 5,795,834 | A * | 8/1998 | Deeb | B32B 27/308 428/354 |
| D472,319 | S * | 3/2003 | Oltmann | A61F 17/00 D24/189 |
| 7,798,323 | B1 * | 9/2010 | McCann | A61F 17/00 206/370 |
| 7,967,139 | B2 * | 6/2011 | Brinker | A61B 50/30 206/472 |
| 8,647,123 | B1 * | 2/2014 | Carter | G16H 40/63 434/262 |
| 9,226,841 | B1 * | 1/2016 | Amodt | A61F 5/05841 |
| 2006/0206047 | A1 * | 9/2006 | Lampe | A61F 13/12 602/42 |
| 2008/0143080 | A1 * | 6/2008 | Burr | D04B 1/246 280/495 |
| 2008/0283426 | A1 * | 11/2008 | Primer | G09F 3/0289 206/570 |

(Continued)

*Primary Examiner* — Jacob K Ackun
(74) *Attorney, Agent, or Firm* — Workman Nydegger

(57) ABSTRACT

A first aid medical treatment apparatus, wherein the apparatus' case and duct tape allow for efficient and easy use and creation of different bandages without necessitating every type of bandage being part of the first aid kit.

18 Claims, 7 Drawing Sheets

(56) References Cited

U.S. PATENT DOCUMENTS

| | | | | |
|---|---|---|---|---|
| 2009/0205996 A1* | 8/2009 | Celis | A45F 5/00 | 206/570 |
| 2010/0274205 A1* | 10/2010 | Morelli | A61B 50/30 | 604/290 |
| 2011/0005646 A1* | 1/2011 | Nelson | A45C 1/024 | 150/103 |
| 2011/0029009 A1* | 2/2011 | Dietl | F41C 27/00 | 40/672 |
| 2012/0067768 A1* | 3/2012 | Jaeger | A61F 17/00 | 206/570 |
| 2012/0158041 A1* | 6/2012 | Craig | A61B 17/1322 | 2/2.5 |
| 2013/0138055 A1* | 5/2013 | Samlaska | A61L 15/42 | 604/307 |
| 2013/0237790 A1* | 9/2013 | Riess | A61B 5/291 | 600/373 |
| 2013/0299383 A1* | 11/2013 | Hernandez | B25H 5/00 | 206/570 |
| 2014/0061273 A1* | 3/2014 | Bullivant | A45F 3/04 | 224/576 |
| 2015/0027922 A1* | 1/2015 | Fresco | A61F 17/00 | 206/570 |
| 2015/0099412 A1* | 4/2015 | Elafros | C09J 7/29 | 428/323 |
| 2016/0045381 A1* | 2/2016 | Spence | A61F 17/00 | 206/570 |
| 2016/0184148 A1* | 6/2016 | Johnson | A61B 50/30 | 206/570 |
| 2017/0361550 A1* | 12/2017 | Hager | B32B 3/02 | |
| 2019/0180599 A1* | 6/2019 | Kemp | G06Q 10/087 | |
| 2019/0282406 A1* | 9/2019 | Ambartsoumian | A61F 13/0269 | |
| 2020/0022474 A1* | 1/2020 | Tyler | A45C 5/03 | |
| 2020/0140721 A1* | 5/2020 | Gross | C09J 7/201 | |
| 2020/0383742 A1* | 12/2020 | Dean | A61B 46/20 | |
| 2020/0383744 A1* | 12/2020 | Mithani | A61B 46/20 | |

\* cited by examiner

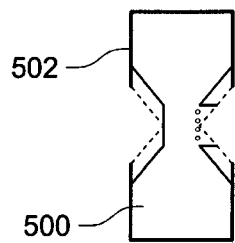
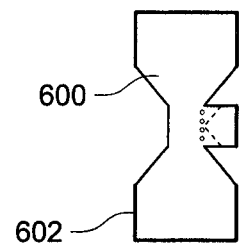
FIG. 5  FIG. 6
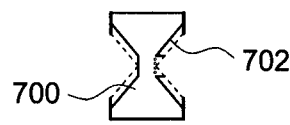
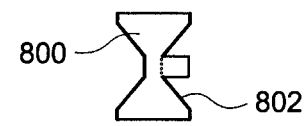
FIG. 7  FIG. 8
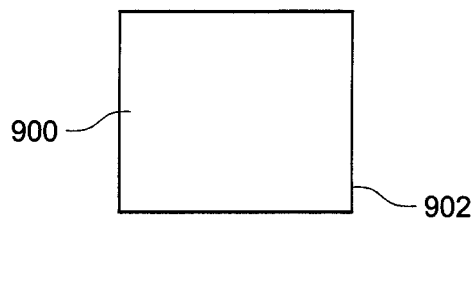
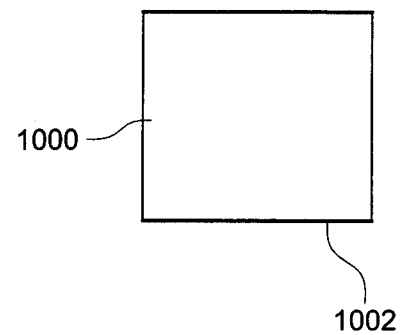
FIG. 9  FIG. 10
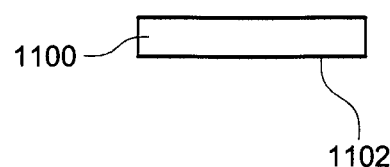
FIG. 11

FIRST AID MEDICAL TREATMENT APPARATUS AND METHOD

CROSS-REFERENCE TO RELATED APPLICATIONS

This application claims the benefit of U.S. Provisional Application Ser. No. 62/851,621, filed on May 22, 2019, which is incorporated herein by reference.

TECHNICAL FIELD

The present disclosure relates to first aid kits and, more particularly, portable first aid kits.

BACKGROUND

First aid kits are a necessity for many businesses and individuals to help ensure that emergency care be given immediately to an injured person. A first aid kit may minimize injury and future disability, or problems associated with injuries. In more serious cases, where major wounds occur, first aid kits can be necessary to keep an injured person alive so that more extensive treatment may be provided in locations where medical personnel provide more extensive treatments, such as tents, clinics, hospitals, medical aircraft or boat, etc.

Often these kits may contain various items and be referred to as survival kits or mini survival kits, which, as the names imply, contain basic medical equipment in order to provide emergency care to injured persons The survival industry has increased over the past few decades, with over half of American households having a first aid kit. But many of the first aid kits possessed by individuals and families are very heavy or bulky, and thus are not easily transported for use when camping, hiking, biking, or performing other individual or group activities outdoors.

Duct tape is ubiquitous in the United States of America. While originally produced to seal joints in heating or air-conditioning units, it is now used for many different applications—once being used to make entire prom outfits. Its uses seem to only be limited by the imagination and ingenuity of people. Duct tape has a non-adhesive side, usually made from cloth with a polyethylene coating, and a pressure-sensitive adhesive side, usually made from rubber-based adhesives or other adhesives such as hot melt, hide glue, liquid-based glue, epoxy, silicon based adhesives, acrylics, ceramics, urethanes, cyanoacrylates, ultraviolet curing, rubber, synthetic rubber, polyurethane, radiation cured, thermosetting, elastomeric, ethylene vinyl acetate, waterproof, hydrocolloids, or other similar adhesives. There are many varieties of duct tape including waterproof, colored, and duct tape with variable adhesiveness.

Duct tape can easily be cut into various shapes and be torn because of its non-adhesive cloth side. This attribute makes duct tape suitable for making various bandage shapes for first aid kits. However, Duct Tape was not made for use on humans. Surgical tape is a type of pressure-sensitive adhesive tape which usually has a hypoallergenic adhesive designed to hold firmly onto skin without damaging the skin upon removal.

For the foregoing reasons, and others, there is a need for a safe, portable first aid kit that can be used to create necessary bandages depending on the needs of users.

SUMMARY OF EXAMPLE EMBODIMENTS

In one embodiment, a first aid medical treatment apparatus comprises a case and a roll of duct tape.

In one embodiment, a first aid medical treatment apparatus comprises a case and a roll of duct tape, said case designed to fit within any sized roll of duct tape.

In one embodiment, a first aid medical treatment apparatus comprises a case, tape, and first aid supplies, said case comprises compartments for first aid supplies, said case designed to fit within the cylinder of a roll of tape.

In one embodiment, first aid medical treatment apparatus comprises a case, duct tape, and first aid supplies, said case comprises cloth or plastic, said duct tape comprises a cylinder and tape spooled around the circumference of said cylinder, said tape comprises a non-adhesive side of cloth or similar material and a rubber-based adhesive side, said case being of a size to fit within the duct tape's cylinder and first aid supplies within the case.

In one embodiment, a first aid medical treatment apparatus comprises a case, tape, and first aid supplies, said case made from cloth or plastic materials and designed to hold various first aid supplies in various compartments, said case formed to removably couple with the tape.

In one embodiment, a first aid medical treatment apparatus comprises a case, tape, and first aid supplies, the case comprises a top cylinder and a bottom cylinder, the cylinders, having compartments for first aid supplies.

In one embodiment, a first aid medical treatment apparatus comprises a case, tape, and first aid supplies, said case having an inner compartment and an outer compartment, said compartments having first aid supplies stored in or throughout the compartments, designed to be used with the tape or any other components or supplies contained therein.

In one embodiment a first aid medical treatment apparatus comprising a case, tape, and first aid supplies, the case being made of metal, a metal composite, plastic, plastic composite, or any other appropriate substance or combination of substances.

In one embodiment a first aid medical treatment apparatus comprises a case and tape, the tape comprising a non-adhesive side and an adhesive side, such adhesive side comprising medical grade adhesive.

In one embodiment a first aid medical treatment apparatus' roll of tape is printed with a pattern for making various bandages and field dressings from the tape.

In one embodiment a first aid medical treatment apparatus comprises a case, tape, and first aid supplies, the case comprises a rectangular shaped cloth with compartments for first aid supplies, said cloth may be rolled up with the supplies to form the case.

In one embodiment, a first aid medical treatment apparatus' tape is comprised of hand-tearable material.

In one embodiment, a first aid medical treatment apparatus' tape is duct tape with a pattern on it for making various dressing for medical applications.

In one embodiment, a first aid medical treatment apparatus' tape has a medical grade adhesive and a pattern or patters that allow one to cut out many different sterile bandages for different medical applications.

In one embodiment, a first aid medical treatment apparatus' tape surrounding the kit has a medical grade adhesive, such as acrylic, silicone, zinc oxide, or any adhesive approved by the United States Department of Heath and Human Services for use on humans.

In one embodiment, a first aid medical treatment apparatus comprises a cloth case, tape, and first aid equipment, the case's cloth comprises tightly woven stretch material, including venetian stretch, spandex, or any other material with high elasticity.

In one embodiment, a first aid medical treatment apparatus comprises a cloth case, tape, and first aid equipment the cloth case containing a pattern on it for application as a tourniquet or a sling in a medical emergency.

In one embodiment, a first aid medical treatment apparatus comprises a cloth case, tape, and first aid equipment, the cloth is made from a tightly woven material that may be used to clean water by filtering out rocks and dirt and other small materials when water is poured through the cloth.

In one embodiment, a first aid medical treatment apparatus's cloth case has a compartment at one of its ends, so that the rolled-up case can fit inside the tape's cylinder and be stored easily.

In one embodiment, a first aid medical treatment apparatus comprises a cloth case, tape, and first aid equipment, the cloth comprises three sections, two opposing side sections which form compartments for storing medical, cleaning, sterilizing, or any other type of supplies, and a middle section.

In one embodiment, a first aid medical treatment apparatus's cloth case has a dotted line running along the center of it to show where to cut in order to create a sling.

In one embodiment, a first aid medical treatment apparatus's cloth case has a dotted line running along the center of it to show where to cut in order to create a tourniquet.

In one embodiment, a method of using a first aid medical treatment apparatus comprises determining the type of injury or wound and then determining the bandage that would be appropriate for the injury or wound, unravelling a portion of a roll of tape containing various bandage shapes, using a sharp object or torsion to shape the tape according to the shapes contained thereon, and applying the tape as a bandage to the corresponding wound.

In one embodiment, a method of using a first aid medical treatment apparatus, wherein duct tape is spooled around the circumference of the cylinder, the duct tape having a repeatable pattern indicating common bandage shapes, wherein a user unrolls a portion of the duct tape, and uses a sharp instrument cuts out a pattern shown on the duct tape to fashion a bandage as required, the bandage is then applied to a person's injury or injuries.

In one embodiment, a method of using a first aid medical treatment apparatus comprises a case, tape, and first aid supplies, the tape having a repeatable pattern indicating common bandage shapes, wherein a user unrolls a portion of the tape, and uses a sharp instrument and cuts out a pattern shown on the tape to fashion a bandage as required, the bandage is then applied to a person's injury or injuries.

In one embodiment, a method of using a first aid medical treatment apparatus comprises a case, tape, and first aid supplies, wherein a user unrolls the case and uses a sharp instrument to cut along the pattern shown on the case to fashion a sling as required, and then the sling is applied to a person's injury or injuries.

In one embodiment, a method of using a first aid medical treatment apparatus comprises a case, tape, and first aid supplies, wherein a user unrolls the case and uses a sharp instrument to cut along the pattern shown on the case to fashion a tourniquet as required, and then the tourniquet is applied to a person's injury or injuries.

BRIEF DESCRIPTION OF THE DRAWINGS

FIG. 5 is a top view of the first aid medical treatment apparatus's duct tape non-adhesive side;

FIG. 6 is a top view of the first aid medical treatment apparatus's duct tape non-adhesive side;

FIG. 7 is a top view of the first aid medical treatment apparatus's duct tape non-adhesive side;

FIG. 8 is a top view of the first aid medical treatment apparatus's duct tape non-adhesive side;

FIG. 9 is a top view of the first aid medical treatment apparatus's duct tape non-adhesive side;

FIG. 10 is a top view of the first aid medical treatment apparatus's duct tape non-adhesive side;

FIG. 11 is a top view of the first aid medical treatment apparatus's duct tape non-adhesive side;

DETAILED DESCRIPTION OF EXAMPLE EMBODIMENTS

Figure 1:
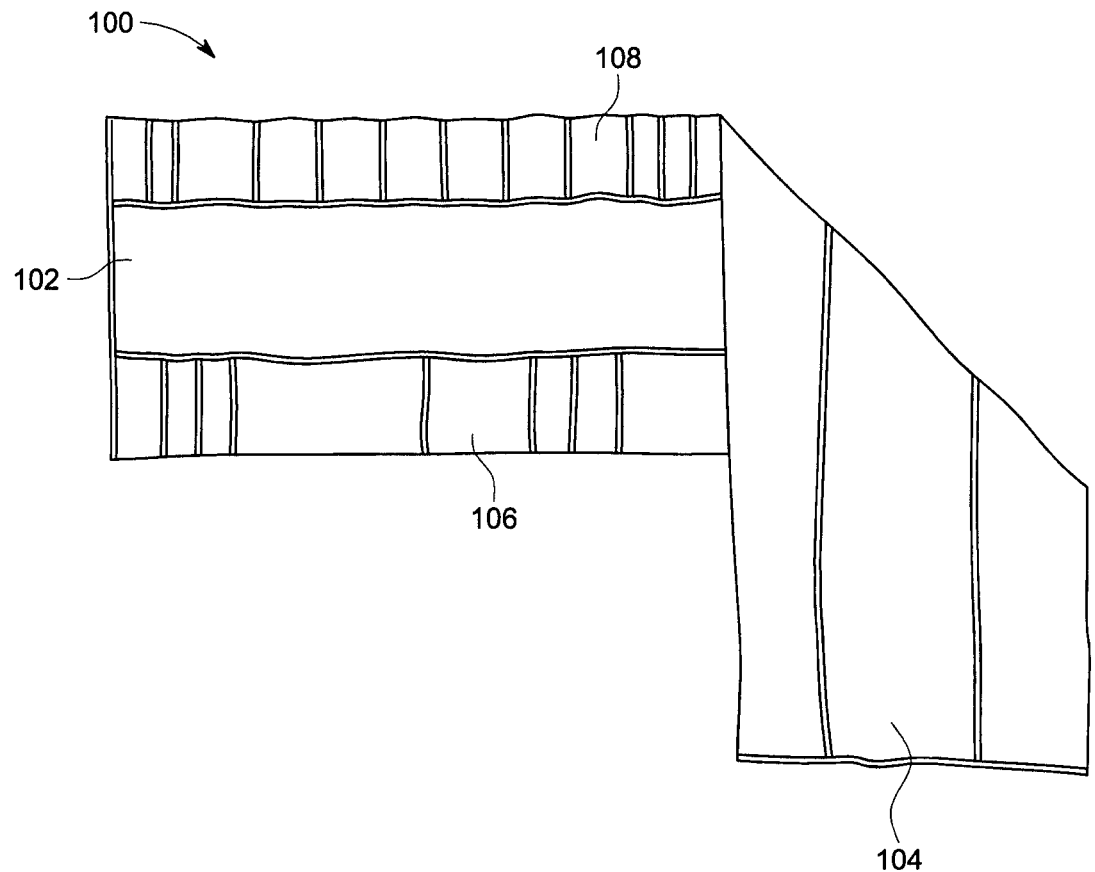
FIG. 1 illustrates a top view of the first aid medical treatment apparatus's case.

The following descriptions depict only example embodiments and are not to be considered limiting in scope. Any reference herein to "the invention" is not intended to restrict or limit the invention to exact features or steps of any one or more of the exemplary embodiments disclosed in the present specification. References to "one embodiment," "an embodiment," "various embodiments," and the like, may indicate that the embodiment(s) so described may include a particular feature, structure, or characteristic, but not every embodiment necessarily includes the particular feature, structure, or characteristic. Further, repeated use of the phrase "in one embodiment," or "in an embodiment," do not necessarily refer to the same embodiment, although they may.

Reference to the drawings is done throughout the disclosure using various numbers. The numbers used are for the convenience of the drafter only and the absence of numbers in an apparent sequence should not be considered limiting and does not imply that additional parts of that particular embodiment exist. Numbering patterns from one embodiment to the other need not imply that each embodiment has similar parts, although it may.

Accordingly, the particular arrangements disclosed are meant to be illustrative only and not limiting as to the scope of the invention, which is to be given the full breadth of the appended claims and any and all equivalents thereof. Although specific terms are employed herein, they are used in a generic and descriptive sense only and not for purposes of limitation. Unless otherwise expressly defined herein, such terms are intended to be given their broad, ordinary, and customary meaning not inconsistent with that applicable in the relevant industry and without restriction to any specific embodiment hereinafter described. As used herein, the article "a" is intended to include one or more items. When used herein to join a list of items, the term "or" denotes at least one of the items but does not exclude a plurality of items of the list. For exemplary methods or processes, the sequence and/or arrangement of steps described herein are illustrative and not restrictive.

It should be understood that the steps of any such processes or methods are not limited to being carried out in any particular sequence, arrangement, or with any particular graphics or interface. Indeed, the steps of the disclosed processes or methods generally may be carried out in various sequences and arrangements while still falling within the scope of the present invention.

The term "coupled" may mean that two or more elements are in direct physical contact. However, "coupled" may also mean that two or more elements are not in direct contact with each other, but yet still cooperate or interact with each other.

The terms "comprising," "including," "having," and the like, as used with respect to embodiments, are synonymous, and are generally intended as "open" terms (e.g., the term "including" should be interpreted as "including, but not limited to," the term "having" should be interpreted as "having at least," the term "includes" should be interpreted as "includes, but is not limited to," etc.).

The term "duct tape," as used with respect to embodiments, are synonymous with medical grade duct tape, or duct tape with an adhesive that may be used on humans.

As previously discussed, there is a need for a safe, portable first aid kit that can be used to create necessary bandages depending on the needs of users.

In one embodiment, a first aid medical treatment apparatus comprises a roll of duct tape and a case which may be placed in an enclosure for easy transport.

In one embodiment, as shown in FIG. 1, a first aid medical treatment apparatus's case 100 comprises a first side 102 and a second side 104, the first side 102 configured to form different sized compartments 106 and 108, such compartments formed to hold different types of items (not shown), when filled with various items, the case 100 may be rolled up, side 102 forming the inside and second side 104 forming the outside of the case 100.

Figure 2:
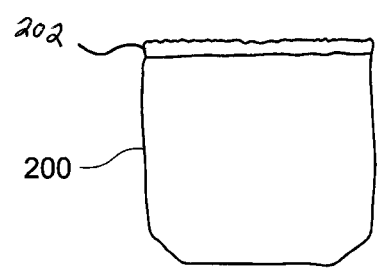
FIG. 2 illustrates a side view of an enclosure for the first aid medical treatment apparatus.

In one embodiment, as shown in FIG. 2, an enclosure 200 for the first aid medical treatment apparatus comprises an enclosure and an opening 202.

Figure 3:
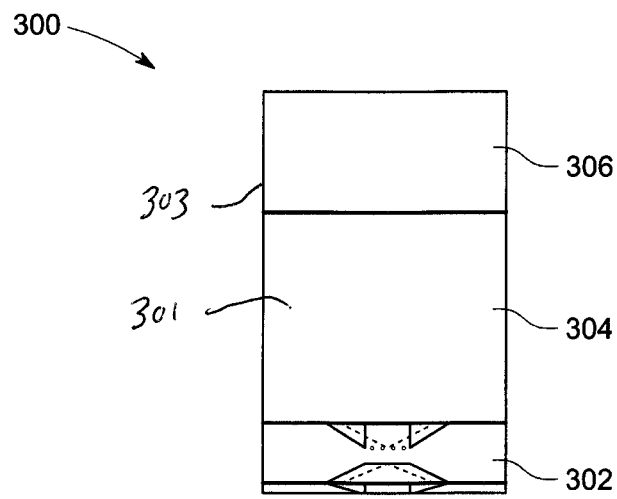
FIG. 3 is a top view of the first aid medical treatment apparatus's duct tape non-adhesive side.

In one embodiment, as shown in FIG. 3, a first aid medical treatment apparatus's duct tape 300 comprises a non-adhesive layer 301 and an adhesive layer 303, said non-adhesive layer 301 comprises various patterns such as a butterfly bandage 302, a medium dressing 304, and a small dressing 306, whereby the patterns are used to gauge the appropriate bandage to be used.

Figure 4:
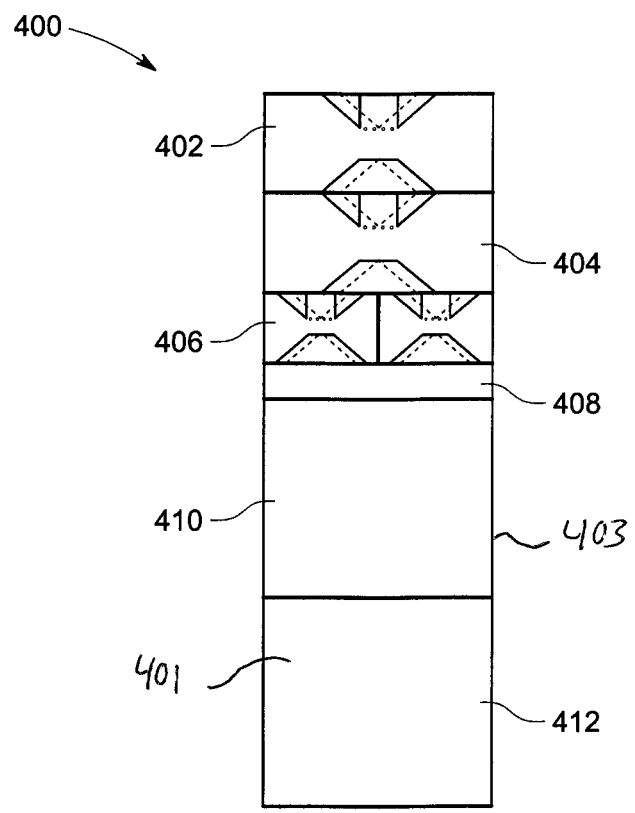
FIG. 4 is a top view of the first aid medical treatment apparatus's duct tape non-adhesive side.

In one embodiment, as shown in FIG. 4, a first aid medical treatment apparatus's duct tape section 400 comprises a non-adhesive layer 401 and an adhesive layer 403, the duct tape section 400 showing a repeatable pattern of various bandages such as a butterfly bandage 402, another butterfly bandage 404, two small butterfly bandages 406, a small dressing 408, a medium dressing 410, and another dressing 412, whereby the user determines the need and, using the appropriate bandage pattern, cuts along the pattern and applies the bandage to a wound.

In one embodiment, as shown in FIGS. 5-11, a first aid medical treatment apparatus's duct tape bandages all having an adhesive side 502 602 702 802 902 1002 1102, and a non-adhesive side 500 600 700 800 900 1000 1100, with butterfly bandages 500 600, small butterfly bandages 700 800, medium dressings 900 1000 and a small dressing 1100, each represents a portion of the duct tape's pattern separated from the roll of duct tape (not shown).

Figure 12:
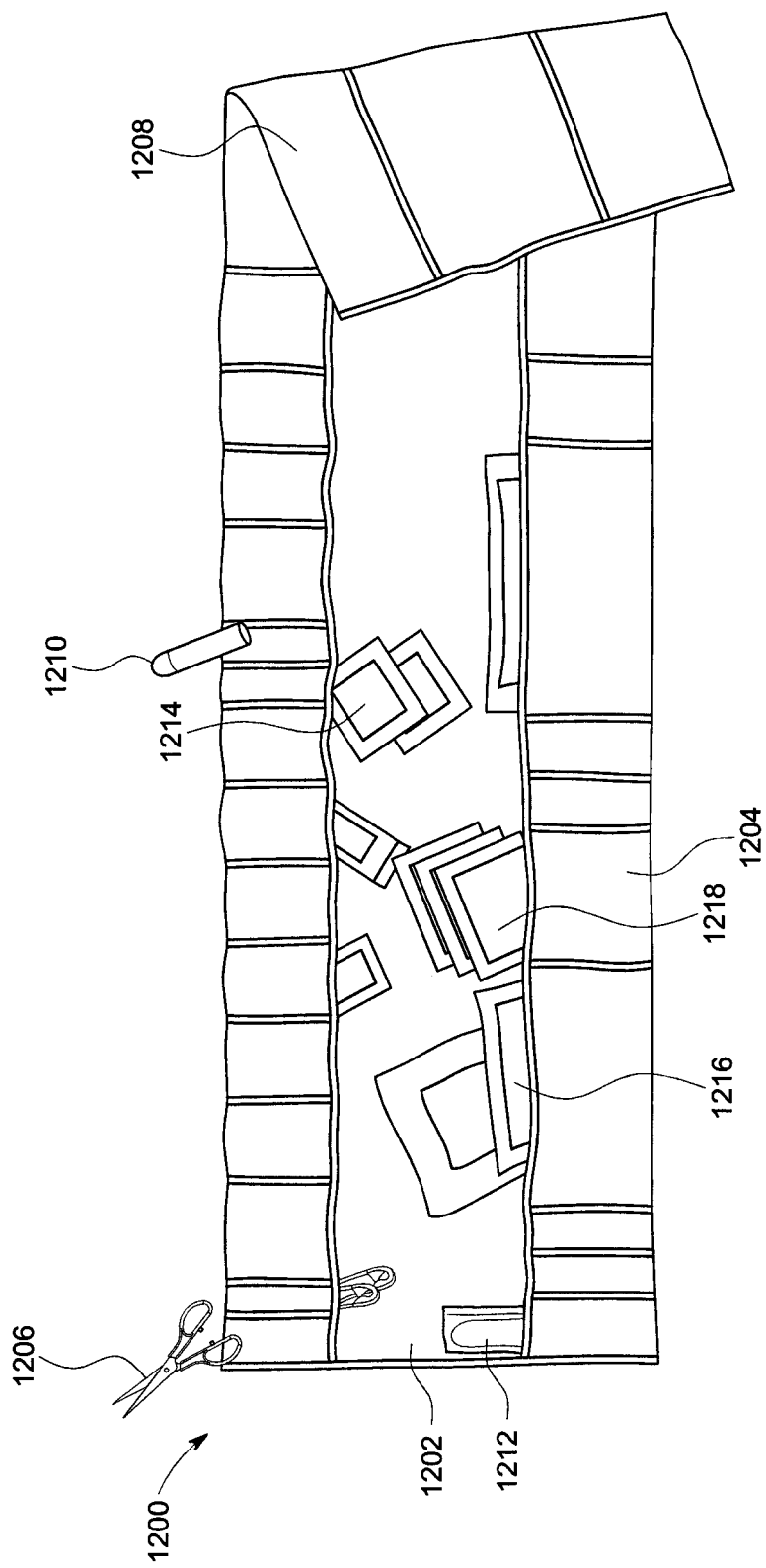
FIG. 12 is top view of the first aid medical treatment apparatus's case.

In one embodiment, as shown in FIG. 12, a first aid medical treatment apparatus's case 1200 unrolled having a first side 1202 and a second side 1208, said first side 1202 containing at least one pocket 1204 and common first aid items such as scissors 1206, a puncture wound plug 1210, a tongue depressor 1212, an alcohol pad 1214, a non-adherent pad 1216, a gauze pad 1218, among other first aid items such as medicines (not shown) and other items common to first aid kits (not shown), the case 1200, in this embodiment having many-sized compartments conforming to various shapes and sizes of first aid items.

Figure 13:
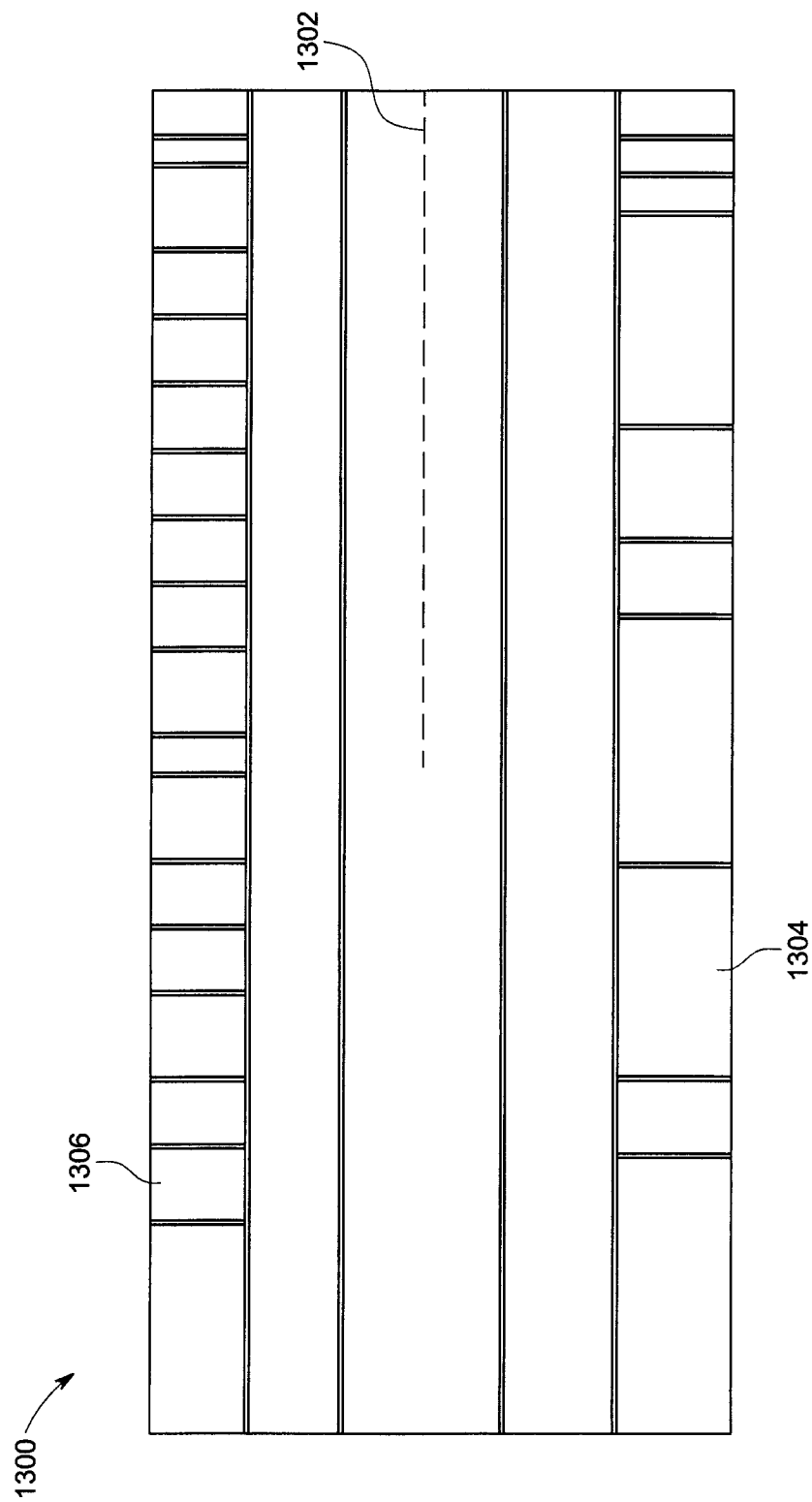
FIG. 13 is top view of the first aid medical treatment apparatus's case apparatus.

In one embodiment, as shown in FIG. 13, a first aid medical treatment apparatus's case 1300 having many pocket sizes a small pocket 1306 and a large pocket 1304, and many other compartments (not numbered individually) in a pattern shown on the case 1300, a cut-line 1302 on the case 1300 indicating the location to cut the case in order to create a tourniquet or sling.

Figure 14:
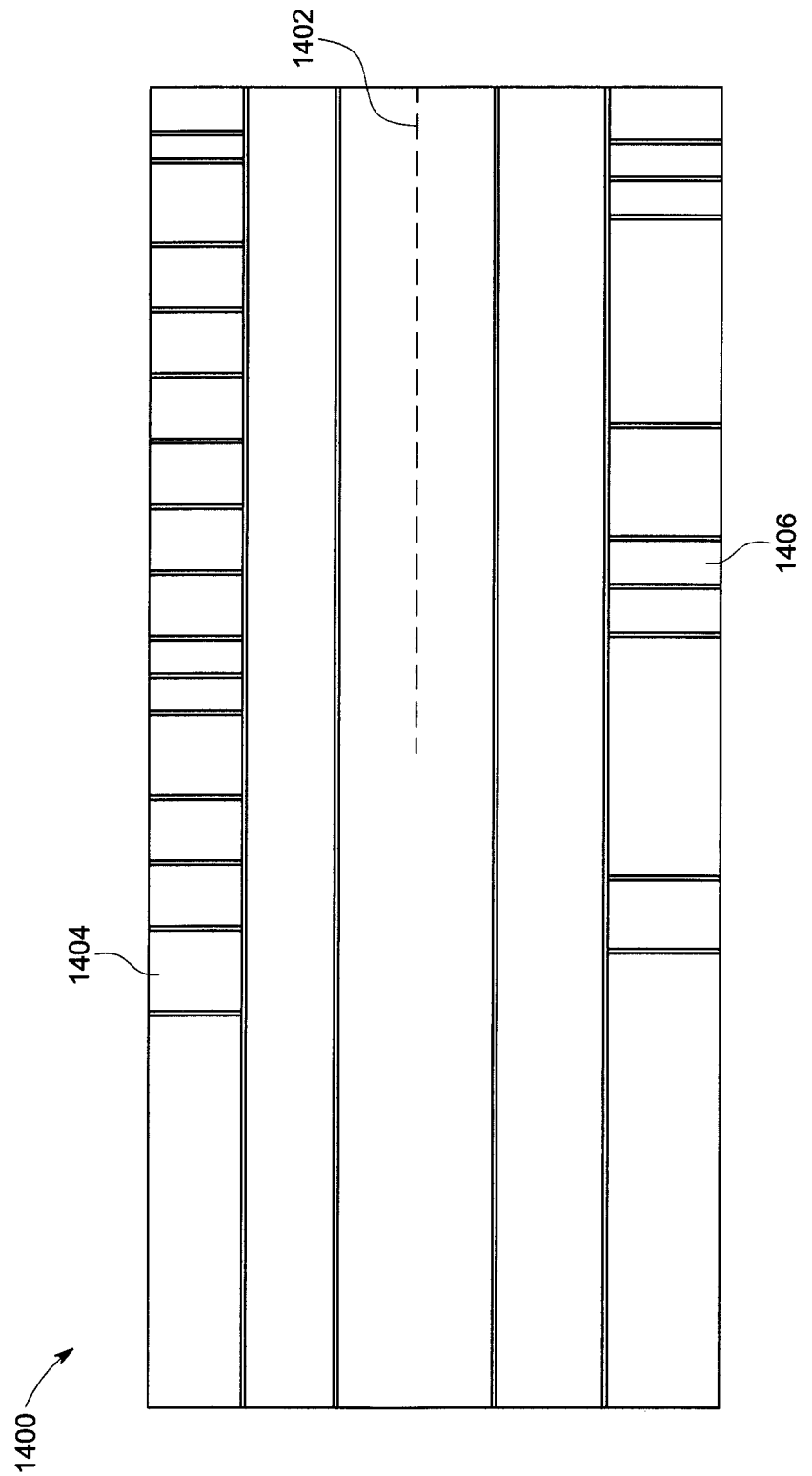
FIG. 14 is top view of the first aid medical treatment apparatus's case.

In one embodiment, as shown in FIG. 14, a first aid medical treatment apparatus's case 1400 having many pocket sizes a small pocket 1406 and a large pocket 1404, and many other compartments (not numbered individually) in a pattern shown on the case 1400, a cut-line 1402 on the case 1400 indicating the location to cut the case in order to create a tourniquet or sling.

Figure 15:
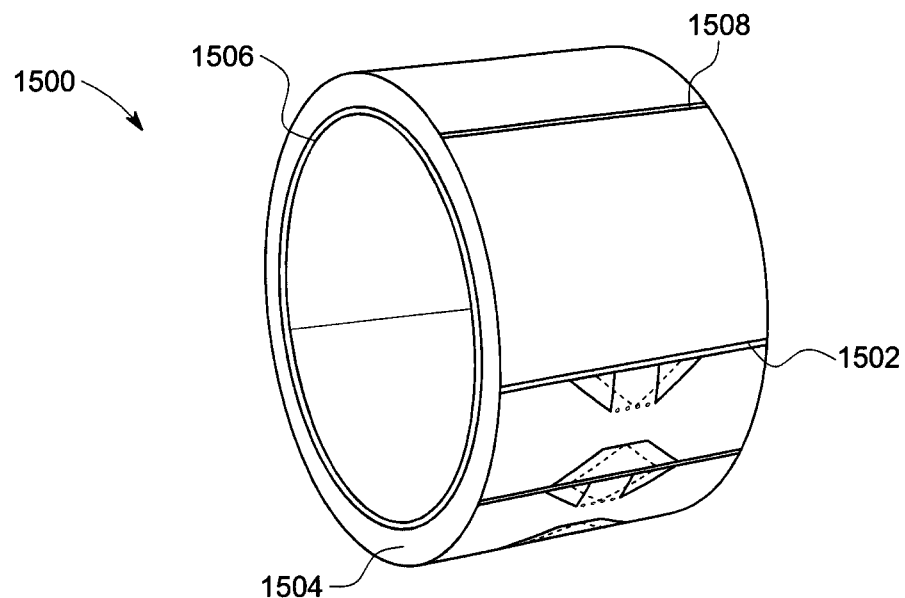
FIG. 15 is a perspective side view of the first aid medical treatment apparatus's duct tape.

In one embodiment, as shown in FIG. 15, a first aid medical treatment apparatus's duct tape 1500 having a non-adhesive layer 1502 and an adhesive layer 1504, the non-adhesive layer 1502 containing patterns indicated in previous figures, a cylinder 1506 for the duct tape 1500 of a size allowing for a rolled up case (not shown) to fit within the cylinder 1506.

Figure 16:
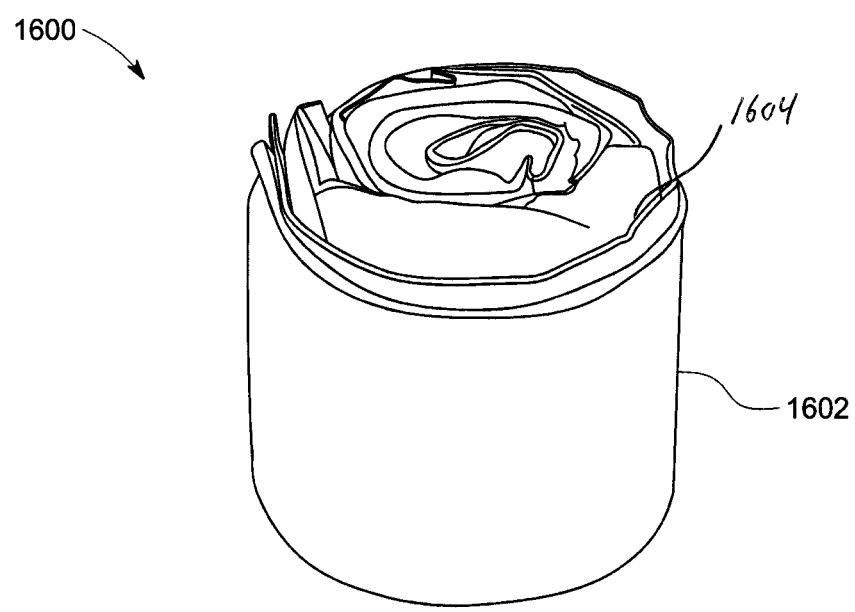
FIG. 16 is an perspective top view of the first aid medical treatment apparatus's case.

In one embodiment, as shown in FIG. 16, a first aid medical treatment apparatus's case 1600 shown rolled up with the outside layer 1602 and an inside layer 1604, the inside layer 1604 having various compartments and first aid supplies (not shown).

In one embodiment, a method of using a first aid medical treatment apparatus comprises assessing a wound, determining the wound requires irrigation with a syringe or injection of medication with a syringe, separating the first aid medical treatment apparatus, putting water or medicine in the space created, reassembling said apparatus, removing a plastic cap from said apparatus's small opening, attaching an irrigation top or needle to said small opening, positioning the irrigation top above the wound or inserting the needle into the wounded person's body, and compressing the apparatus's lid to irrigate the wound or to inject medicine into the wounded person's body.

In one embodiment, a method of using a first aid medical treatment apparatus comprises a cylinder, a backing, a removable lid, wherein duct tape is spooled around the circumference of the cylinder, the duct tape having a repeatable pattern indicating common bandage shapes, wherein a user unrolls a portion of the duct tape, and uses a sharp instrument cuts out a pattern shown on the duct tape to fashion a bandage as required, the bandage is then applied to a person's injury or injuries.

In one embodiment, a method of using a first aid medical treatment apparatus comprises a case, tape, and first aid supplies, the tape having a repeatable pattern indicating common bandage shapes, wherein a user unrolls a portion of the tape, and uses a sharp instrument and cuts out a pattern shown on the tape to fashion a bandage as required, the bandage is then applied to a person's injury or injuries.

In one embodiment, a method of using a first aid medical treatment apparatus comprises a case, tape, and first aid supplies, wherein a user unrolls the case and uses a sharp instrument to cut along the pattern shown on the case to fashion a sling as required, and then the sling is applied to a person's injury or injuries.

In one embodiment, not shown here, a first aid medical treatment apparatus comprises a case, tape, and first aid supplies in one unit wherein portions of the apparatus are not removable but are separable, and combinable.

In one embodiment, a method of using a first aid medical treatment apparatus comprises a case, tape, and first aid supplies, wherein a user unrolls the case and uses a sharp instrument to cut along the pattern shown on the case to fashion a tourniquet as required, and then the tourniquet is applied to a person's injury or injuries.

In one embodiment, a method of using a first aid medical treatment apparatus comprises a case, tape, and first aid supplies, the case comprises a top cylinder and a bottom cylinder, each cylinder comprises a plate and a ring, the plate having a diameter slightly larger than the ring thus creating a flange, the bottom cylinder's plate having a hole in its center to allow substances, usually liquids, to flow into and out of the space between it and the top cylinder, the bottom cylinder acting as the cylindrical tube or barrel of a syringe, and the top cylinder acting as the plunger of a syringe, wherein a user adds liquid, medicine, or both to the space between the top and bottom cylinders, the user pushes the cylinders together to apply a wound as required.

In one embodiment, a method of using a first aid medical treatment apparatus comprises a case, tape, and first aid supplies, the case comprises a top cylinder and a bottom cylinder, each cylinder comprises a plate and a ring, the plate having a diameter slightly larger than the ring thus creating a flange, the bottom cylinder's plate having a hole in its center to allow substances, usually liquids, to flow into and out of the space between it and the top cylinder, the bottom cylinder acting as the cylindrical tube or barrel of a syringe, and the top cylinder acting as the plunger of a syringe, wherein a user removes a needle from the first aid supplies, attaches the needle to the hole in the bottom cylinder, adds liquid, medicine, or both to the space between the top and bottom cylinders, then the user inserts the needle into an injured person and pushes the cylinders together to inject into the injured person.

It is appreciated that the first aid medical treatment apparatus allows a user to have a readily available first aid kit within a roll or tape, thus allowing for multiple items to be positioned into the apparatus, while still allowing for said apparatus to provide various functionality such as syringe-type functionality, and have a plethora of bandage types and sizes readily available from the tape.

It is appreciated that, although most embodiments have shown cylindrical portions which are separated from each other, the roll of tape could also be one piece which is separable but not removable from the other portions of the first aid medical treatment apparatus.

Exemplary embodiments are described above. No element, act, or instruction used in this description should be construed as important, necessary, critical, or essential unless explicitly described as such. Although only a few of the exemplary embodiments have been described in detain herein, those skilled in the art will readily appreciate that many modifications are possible in these exemplary embodiments without materially departing from the novel teachings and advantages herein. Accordingly, all such modifications are intended to be included within the scope of this invention.

What is claimed is:

1. A first aid medical treatment apparatus comprising:
a roll of tape comprising:
a non-adhesive side having one or more patterns thereon of one or more bandages or field dressings, the tape being configured to be torn or cut along the one or more patterns to create one or more individual bandages or field dressings from the tape;
an adhesive side, the adhesive side comprising a medical grade adhesive; and
a cavity with at least one opening to a side of the roll of tape; and
a case having a plurality of compartments configured to hold a plurality of first aid items, the case being configured to be selectively rolled up into a storage configuration and selectively unrolled to an unrolled configuration to provide access to the plurality of compartments, the case being sized such that that case can be disposed within the cavity in the tape when the case is in the storage configuration.

2. The first aid medical treatment apparatus of claim 1, wherein the one or more patterns comprise patterns of a plurality of different styles of bandages or field dressings.

3. The first aid medical treatment apparatus of claim 1, wherein the one or more patterns comprises patterns of a plurality of different sized bandages or field dressings.

4. The first aid medical treatment apparatus of claim 1, wherein the medical grade adhesive comprises acrylic, silicone, or zinc oxide.

5. The first aid medical treatment apparatus of claim 1, wherein the case comprises a first side and an opposing second side, the first side comprising the plurality of compartments.

6. The first aid medical treatment apparatus of claim 5, wherein the plurality of compartments are arranged in a top row and a bottom row along a length of the case.

7. The first aid medical treatment apparatus of claim 6, wherein each of the compartments of the plurality of compartments comprises an opening to an interior thereof, wherein the openings in the compartments of the top row and the openings in the compartments of the bottom row open towards one another.

8. The first aid medical treatment apparatus of claim 1, wherein the plurality of compartments comprise compartments of different sizes.

9. The first aid medical treatment apparatus of claim 1, wherein the non-adhesive side of the tape is formed of a cloth material that is configured to be torn by hand.

10. The first aid medical treatment apparatus of claim 1, wherein the case comprises one or more patterns thereon, the one or more patterns on the case being configured to indicate cut lines that can be cut to transform the case into a tourniquet or sling.

11. The first aid medical treatment apparatus of claim 10, wherein the one or more patterns on the case comprise a line running along a center portion thereof.

12. The first aid medical treatment apparatus of claim 1, further comprising an enclosure that is configured to receive therein the roll of tape and the case when the case is disposed within the cavity of the tape.

13. A first aid medical treatment apparatus comprising:
a roll of tape comprising:
a non-adhesive side having one or more patterns thereon of a plurality of bandages or field dressings, the non-adhesive side comprising a cloth material that is configured to be torn by hand along the one or more patterns to create individual bandages or field dressings from the tape;
an adhesive side, the adhesive side comprising a medical grade adhesive; and
a cavity with at least one opening to a side of the roll of tape;
a case having a first side and an opposing second side, the first side comprising a plurality of compartments configured to hold a plurality of first aid items, the case being configured to be selectively rolled up into a storage configuration and selectively unrolled to an unrolled configuration to provide access to the plurality of compartments, the case being sized such that that case can be disposed within the cavity in the tape when the case is in the storage configuration; and
an enclosure that is configured to receive therein the roll of tape and the case when the case is disposed within the cavity of the tape.

14. The first aid medical treatment apparatus of claim 13, wherein the one or more patterns comprise patterns of a plurality of different styles of bandages or field dressings.

15. The first aid medical treatment apparatus of claim 13, wherein the one or more patterns comprises patterns of a plurality of different sized bandages or field dressings.

16. The first aid medical treatment apparatus of claim 13, wherein the medical grade adhesive comprises acrylic, silicone, or zinc oxide.

17. The first aid medical treatment apparatus of claim 13, wherein the case comprises a first side and an opposing second side, the first side comprising the plurality of compartments arranged in a top row and a bottom row along a length of the case.

18. A first aid medical treatment apparatus comprising:
a roll of tape comprising:
a non-adhesive side having a plurality of patterns thereon of a plurality of bandages or field dressings, the plurality of patterns comprising patterns of a plurality of different styles or sizes of bandages or field dressings, the non-adhesive side comprising a cloth material that is configured to be torn by hand along the plurality of patterns to create individual bandages or field dressings from the tape;
an adhesive side, the adhesive side comprising a medical grade adhesive selected from the group consisting of acrylic, silicone, or zinc oxide; and
a cavity with at least one opening to a side of the roll of tape;
a case having a first side and an opposing second side, the first side comprising a plurality of compartments configured to hold a plurality of first aid items, the plurality of compartments being arranged in a first row along a first edge of the case and a second row along a second edge of the case, each of the compartments having an opening therein, the case comprising one or more patterns thereon and configured to indicate cut lines that can be cut to transform the case into a tourniquet or sling, the case being configured to be selectively rolled up into a storage configuration and selectively unrolled to an unrolled configuration to provide access to the plurality of compartments, the case being sized such that that case can be disposed within the cavity in the tape when the case is in the storage configuration; and
an enclosure that is configured to receive therein the roll of tape and the case when the case is disposed within the cavity of the tape.

* * * * *